(12) United States Patent
Blau et al.

(10) Patent No.: US 11,597,976 B2
(45) Date of Patent: Mar. 7, 2023

(54) IDENTIFICATION OF TELOMERE LENGTH AS A DIAGNOSTIC BIOMARKER FOR HERITABLE CARDIOMYOPATHIES

(71) Applicant: The Board of Trustees of the Leland Stanford Junior University, Stanford, CA (US)

(72) Inventors: Helen M. Blau, Menlo Park, CA (US); Chia Yu Alex Chang, Palo Alto, CA (US)

(73) Assignee: The Board of Trustees of the Leland Stanford Junior University, Stanford, CA (US)

(*) Notice: Subject to any disclaimer, the term of this patent is extended or adjusted under 35 U.S.C. 154(b) by 1185 days.

(21) Appl. No.: 16/078,486

(22) PCT Filed: Feb. 22, 2017

(86) PCT No.: PCT/US2017/018845
§ 371 (c)(1),
(2) Date: Aug. 21, 2018

(87) PCT Pub. No.: WO2017/147132
PCT Pub. Date: Aug. 31, 2017

(65) Prior Publication Data
US 2019/0048420 A1 Feb. 14, 2019

Related U.S. Application Data

(60) Provisional application No. 62/298,334, filed on Feb. 22, 2016.

(51) Int. Cl.
*C07H 21/02* (2006.01)
*C12Q 1/6883* (2018.01)
*C12Q 1/68* (2018.01)

(52) U.S. Cl.
CPC .......... *C12Q 1/6883* (2013.01); *C12Q 1/68* (2013.01); *C12Q 2600/136* (2013.01); *C12Q 2600/156* (2013.01)

(58) Field of Classification Search
CPC ................ C12Q 2600/136; C12Q 1/6883
See application file for complete search history.

(56) References Cited

FOREIGN PATENT DOCUMENTS

WO 2013/013206 A1 1/2013
WO 2016/020346 A1 2/2016

OTHER PUBLICATIONS

Moslehi et al. (Circ Res, 2012, 110, 1226-1237).*
Rajala et al. (Stem Cells International, 2011, 1-12).*
Dambrot et al. (Biochem J, 2011, 434, 25-35).*
Oh et al. (PNAS, 2003, 100, 9, 5378-5383).*
Sehnert et al. (Nature Genetics, 31, 2002, 106-110).*
Sommese et al. (PLOS ONE, 2013, 8, 12, e83403, 1-10).*
Morimoto (Cardiovascular Research, 2008, 77, 659-666).*
Fayssoil et al. (Heart Fail Rev, 2010, 15, 103-107).*
McNally et al., "Genetic mutations and mechanisms in dilated cardiomyopathy", J Clin Invest., Jan. 2, 2013, pp. 19-26,123, American Society for Clinical Investigation, Ann Arbor, MI.
Lapidos et al., "The dystrophin glycoprotein complex: signaling strength and integrity for the sarcolemma", Circ Res., Apr. 30, 2004, pp. 1023-1031, vol. 94, Issue 8, American Heart Association, Inc., Dallas, TX.
Knoll et al., "The cardiac mechanical stretch sensor machinery involves a Z disc complex that is defective in a subset of human dilated cardiomyopathy", Cell, Dec. 27, 2002, pp. 943-955, vol. 111, Issue 7, Elsevier, New York City, NY.
Kamisago et al., "Mutations in Sarcomere Protein Genes as a Cause of Dilated Cardiomyopathy", N Engl J Med., Dec. 7, 2000, pp. 1688-1696, 343, Massachusetts Medical Society, Waltham, MA.
Bienengraeber et al., "ABCC9 mutations identified in human dilated cardiomyopathy disrupt catalytic KATP channel gating" Nat Genet., Apr. 2004, pp. 382-387, vol. 36, No. 4, Springer, Berlin, Germany.
Schmitt et al., "Dilated cardiomyopathy and heart failure caused by a mutation in phospholamban", Science, Feb. 28, 2003, pp. 1410-1413, vol. 299, Issue 5611, American Association for the Advancement of Science, Washington, D.C.
Mourkioti et al., "Role of telomere dysfunction in cardiac failure in Duchenne muscular dystrophy", Nat Cell Biol., Aug. 2013, pp. 895-904, 15(8), Springer, Berlin, Germany.
Bergmann et al., "Evidence for cardiomyocyte renewal in humans", Science, Apr. 3, 2009, pp. 98-102, vol. 324, Issue 5923, American Association for the Advancement of Science, Washington, D.C.
Sun et al., "Patient-Specific Induced Pluripotent Stem Cells as a Model for Familial Dilated Cardiomyopathy", Sci Transl Med., Apr. 18, 2012, pp. 130ra47-130ra47, vol. 4, Issue 130, American Association for the Advancement of Science, Washington, D.C.
Herman et al., "Truncations of titin causing dilated cardiomyopathy", N Engl J Med., Feb. 16, 2012, pp. 619-628, 366, Massachusetts Medical Society, Waltham, MA.
Hinson et al., "Titin mutations in iPS cells define sarcomere insufficiency as a cause of dilated cardiomyopathy", Science, Aug. 28, 2015, pp. 982-986, vol. 349, Issue 6251, American Association for the Advancement of Science, Washington, D.C.
Sahin et al., "Telomere dysfunction induces metabolic and mitochondrial compromise", Nature, Feb. 17, 2011, pp. 359-365, 470, Springer, Berlin, Germany.
Moslehi et al., "Telomeres and Mitochondria in the Aging Heart. Circulation Research", Apr. 27, 2012, pp. 1226-1237, vol. 110, Issue 9, American Heart Association, Inc., Dallas, TX.
Mestroni et al., "Genetic causes of dilated cardiomyopathy", Progress in Pediatric Cardiology, Dec. 2014, pp. 13-18, vol. 37, Issues 1-2, Elsevier, New York City, NY.

* cited by examiner

*Primary Examiner* — Amy H Bowman
(74) *Attorney, Agent, or Firm* — Pamela J. Sherwood; Bozicevic, Field & Francis LLP (57) ABSTRACT

Shortened telomeres are diagnostic of genetic predisposition to cardiomyopathies, e.g. those related to defects in structural proteins expressed in cardiomyocytes.

1 Claim, 7 Drawing Sheets
(7 of 7 Drawing Sheet(s) Filed in Color)

IDENTIFICATION OF TELOMERE LENGTH AS A DIAGNOSTIC BIOMARKER FOR HERITABLE CARDIOMYOPATHIES

CROSS REFERENCE

This is a 371 application and claims the benefit of PCT Application No. PCT/US2017/018845, filed Feb. 22, 2017, which claims benefit of U.S. Provisional Patent Application No. 62/298,334, filed Feb. 22, 2016, which applications are incorporated herein by reference in their entirety.

STATEMENT REGARDING FEDERALLY SPONSORED RESEARCH

This invention was made with Government support under contract AR063963 awarded by the National Institutes of Health. The Government has certain rights in the invention.

BACKGROUND OF THE INVENTION

Cardiomyopathies are defined as diseases of the myocardium, which cause cardiac dysfunction with heart failure, arrhythmia, and sudden death. Cardiomyopathies represent a major cause of morbidity and mortality in both children and adults and are a frequent indication for cardiac transplantation. Primary cardiomyopathies are diseases intrinsic to the myocardium itself and are classified pathophysiologically. This group includes dilated cardiomyopathy (DCM), hypertrophic cardiomyopathy (HCM), restrictive cardiomyopathy (RCM), arrhythmogenic right ventricular cardiomyopathy (ARVC), and unclassified cardiomyopathy.

Primary cardiomyopathies have been attributed in the familial forms to mutations in the genes encoding cardiomyocyte structural proteins, for example cardiac actin, desmin, δ-sarcoglycan, β-sarcoglycan, dystrophin, cardiac troponin T, lamin A/C, titin, and α-tropomyosin.

Diagnosis and treatment of heritable cardiomopathies are of great interest for clinical and research purposes.
Publications McNally et al. J Clin Invest 123, 19-26 (2013). Lapidos et al. Circ Res 94, 1023-1031 (2004). Knoll et al. Cell 111, 943-955 (2002). Kamisago et al. N Engl J Med 343, 1688-1696 (2000). Bienengraeber et al. Nat Genet 36, 382-387 (2004). Schmitt et al. Science 299, 1410-1413 (2003). Mourkioti et al. Nat Cell Biol 15, 895-904 (2013). Bergmann et al. Science 324, 98-102 (2009). Sun et al. Sci Transl Med 4, 130ra47-130ra47 (2012). Herman et al. N Engl J Med 366, 619-628 (2012). Hinson et al. Science 349, 982-986 (2015). Sahin et al. Nature 470, 359-365 (2011).

SUMMARY OF THE INVENTION

Compositions and methods are provided for the analysis of telomere shortening as a marker for heritable cardiomyopathies. In some embodiments of the invention, the heritable cardiomyopathy is associated with a genetic defect in a cytoskeletal or sarcomeric protein. In some embodiments the structural and sarcomeric protein is one or more of dystrophin (DMD), cardiac troponin T type 2 (TNNT2), lamin A/C (LMNA) or titin (TTN). In some embodiments the heritable cardiomyopathy is a dilated cardiomyopathy (DCM). Embodiments may include analysis of an individual with a known genetic mutation for a cardiomyopathy; analysis of individuals with an unknown genetic mutation for a cardiomyopathy, e.g. familial idiopathic DCM; analysis of an individual with known genetic mutation for a cardiomyopathy with varying severity or penetration.

In some embodiments of the invention, telomere length is analyzed on cardiomyocytes, where cardiomyocytes of an individual with a heritable cardiomyopathy is at least about 10% shorter than a non-affected, gender matched control; at least about 20% shorter, at least about 30% shorter, at least about 40% shorter, at least about 50% shorter and may be at least about 60% shorter or more. In some embodiments of any of the embodiments disclosed herein, average telomere length is determined by qPCR, telo-FISH, or Southern Blot. In some embodiments of any of the embodiments disclosed herein, the individual is a human. In some embodiments of any of the embodiments disclosed herein, said one or more known standards are characterized cell lines.

In some embodiments the cardiomyocytes are obtained from a biopsy sample. In other embodiments the cardiomyocytes are differentiated in vitro from patient-derived induced pluripotent stem cells.

In some embodiments a diagnostic assay is provided for determining whether an individual carries a genetic mutation that predisposes to a cardiomyopathy, including without limitation dilated cardiomyopathy, wherein a somatic cell from the individual, e.g. a fibroblast or a peripheral blood mononuclear cell, is induced to pluripotency to generate an iPS cell. The iPS cell is differentiated in culture to a cardiomyocyte. The telomere length of chromosomes in the cardiomyocyte population is measured, where a decrease in length of at least about 10% or more is indicative of a predisposition to cardiomyopathy.

In some embodiments a method of screening compounds for treatment of cardiomyopathy is provided, where the ability of an agent to decrease the effects of telomere shortening is determined. In related embodiments a candidate agent is screened for the ability to intervene in the telomere-p53-mitochondria signaling axis.

BRIEF DESCRIPTION OF THE DRAWINGS

The invention is best understood from the following detailed description when read in conjunction with the accompanying drawings. The patent or application file contains at least one drawing executed in color. Copies of this patent or patent application publication with color drawing(s) will be provided by the Office upon request and payment of the necessary fee. It is emphasized that, according to common practice, the various features of the drawings are not to-scale. On the contrary, the dimensions of the various features are arbitrarily expanded or reduced for clarity. Included in the drawings are the following figures.

FIG. 1A-1B. DCM cardiomyocytes exhibit telomere shortening. (FIG. 1B) Intensity of telomere staining relative to DAPI is shown for DMD (n=4), TNNT2 (n=1), LMNA (n=13), TTN (n=3) and healthy controls samples (n=3 for DMD, n=1 for TNNT2, n=12 [donor] and 6 [control] for LMNA, and n=3 for TTN). The number of nuclei (N) scored: DMD (N=42, 94, 65, and 72) and controls (N=70, 69, 65), TNNT2 (N=804) and controls (N=121), LMNA (N=540, 366, 345, 473, 316, 272, 303, 266, 313, 247, 130 and 234), transplanted donor hearts (N=887, 465, 424, 409, 398, 582, 542, 543, 195, 234, 133, and 180) and LMNA controls (N=136, 146, 194, 124, 102 and 128), and TTN (N=548, 281 and 55) and controls (N=214, 214, and 93). Scale bars, 10 μm. Statistical differences in primary patient samples were tested using a two-tailed Student's t-test. Statistical differences between the hiPSC and hiPSC-CM groups were analyzed using one-way analysis of variance (ANOVA) tests followed by Sidak's multiple comparison test. All data are shown as the mean±SD. Significant differences were determined as P value <0.05.

FIG. 2A-2B. Sarcomeric DCM mutations do not result in telomere shortening in non-contractile vascular smooth muscle cells. (FIG. 2A) Telomere length (TeIC) was evaluated by immunofluorescence staining relative to DAPI staining in α-smooth muscle actin positive vascular smooth muscle cells in patient cardiac sections. (FIG. 2B) Intensity of telomere staining relative to DAPI is shown DMD (n=4), TNNT2 (n=1), TTN (n=3) and healthy controls samples (n=3 for DMD, n=1 for TNNT2, and n=3 for TTN). Scale bars, 10 μm. Statistical differences in primary patient samples were tested using a two-tailed Student's t-test. Statistical differences between the hiPSC and hiPSC-CM groups were analyzed using one-way analysis of variance (ANOVA) tests followed by Sidak's multiple comparison test. All data are shown as the mean±SD. Significant differences were determined as P value <0.05.

FIG. 3A-3C. DCM patient iPSC-CMs recapitulate 20-40 years of telomere shortening in 30 days in culture. (FIG. 3A) Telomere length (TeIC) was evaluated by immunofluorescence staining relative to DAPI staining in starting hiPSC and in cardiac troponin T positive hiPSC-CMs on day 30 of differentiation. Intensity of telomere staining relative to DAPI is shown for (FIG. 3B) DMD (n=3) and healthy control (n=1), TNNT2 (n=3) and healthy family member control (n=2), and TTN (n=2) with matching isogenic control (n=2). (FIG. 3C) For familial DCMs that only affect contracting cardiomyocyte (DMD, TNNT2, and TTN), telomere lengths in starting hiPSCs were also measured. Scale bars, 10 μm. Statistical differences in primary patient samples were tested using a two-tailed Student's t-test. Statistical differences between the hiPSC and hiPSC-CM groups were analyzed using one-way analysis of variance (ANOVA) tests followed by Sidak's multiple comparison test. All data are shown as the mean±SD. Significant differences were determined as P value <0.05.

FIG. 4A-4B. DMD and TNNT2 iPSC-CMs exhibit DNA damage response. (FIG. 4A) Representative DNA damage 53BP1 staining (green) in iPSC-CMs co-stained with telomeric repeat (red) and DAPI (blue). (FIG. 4B) Percentage total of 53BP1 positive iPSC-CMs are shown for DMD, TNNT2 and control iPSC-CMs (day 30).

FIG. 5A-5E. Shortened telomeres results in p53-mediated mitochondrial dysfunction in DMD hiPSC-CMs. (FIG. 5A) Increased p53 protein (normalized to nuclei), (FIG. 5B) decreased in PGC1α mRNA expression, (FIG. 5C) decreased mitochondrial amount, (FIG. 5D) mitochondrial membrane potential, and (FIG. 5E) decreased mitochondrial respiration were observed in DMD hiPSC-CM compared to control hiPSC-CMs. Statistical differences in primary patient samples were tested using a two-tailed Student's t-test. Statistical differences between the hiPSC and hiPSC-CM groups were analyzed using one-way analysis of variance (ANOVA) tests followed by Sidak's multiple comparison test. All data are shown as the mean±SD. Significant differences were determined as P value <0.05.

DETAILED DESCRIPTION OF THE EMBODIMENTS

This invention provides, inter alia, methods for identifying individuals at risk of developing cardiomyopathies that will benefit from treatment with a telomerase enhancing compound or compounds that interfere with telomere-p53-mitochondria signaling axis, as well as methods for treating these individuals.

General Techniques

The practice of the invention will employ, unless otherwise indicated, conventional techniques in nucleic acid chemistry, molecular biology, microbiology, cell biology, biochemistry, and immunology, which are well known to those skilled in the art. Such techniques are explained fully in the literature, such as, Molecular Cloning: A Laboratory Manual, second edition (Sambrook et al., 1989) and Molecular Cloning: A Laboratory Manual, third edition (Sambrook and Russel, 2001), (jointly referred to herein as "Sambrook"); Current Protocols in Molecular Biology (F. M. Ausubel et al., eds., 1987, including supplements through 2001); PCR: The Polymerase Chain Reaction, (Mullis et al., eds., 1994). Nucleic acids can be synthesized in vitro by well-known chemical synthesis techniques, as described in, e.g., Carruthers (1982) Cold Spring Harbor Symp. Quant. Biol. 47:411-418; Adams (1983) J. Am. Chem. Soc. 105: 661; Belousov (1997) Nucleic Acids Res. 5 25:3440-3444; Frenkel (1995) Free Radic. Biol. Med. 19:373-380; Blommers (1994) Biochemistry 33:7886-7896; Narang (1979) Meth. Enzymol. 68:90; Brown (1979) Meth. Enzymol. 68:109; Beaucage (1981) Tetra. Lett. 22:1859; Komberg and Baker, DNA Replication, 2nd Ed. (Freeman, San Francisco, 1992); Scheit, Nucleotide Analogs (John Wiley, New York, 1980); Uhlmann and Peyman, Chemical Reviews, 90:543-584, 1990.

Definitions

Heritable cardiomyopathies. Cardiomyopathies may include one or more of the following conditions. Dilated cardiomyopathy (DCM). In DCM a portion of the myocardium is dilated, often without any obvious cause. Left or right ventricular systolic pump function of the heart is impaired, leading to progressive cardiac enlargement and hypertrophy, a process called remodeling. About 25-35% of patients have familial forms of the disease, with most mutations affecting genes encoding cytoskeletal proteins, while some affect other proteins involved in contraction, sarcolemma or nuclear envelope. The disease is genetically heterogeneous, but the most common form of its transmission is an autosomal dominant pattern. Cytoskeletal proteins involved in DCM include cardiac troponin T (TNNT2), α-cardiac actin, desmin, δ-sarcoglycan, β-sarcoglycan, dystrophin (DMD), Titin (TTN) and the nuclear lamins A and C (LMNA), and various structural proteins including other contractile, sarcolemmal and nuclear envelope proteins.

Hypertrophic cardiomyopathy (HCM), is a condition in which sarcomeres are increased causing heart muscle cells to increase in size, which results in the thickening of the heart muscle. In addition, the normal alignment of muscle cells is disrupted, a phenomenon known as myocardial disarray. HCM also causes disruptions of the electrical functions of the heart. HCM is most commonly due to a mutation in one of 9 sarcomeric genes that results in a mutated protein in the sarcomere. Myosin heavy chain mutations are associated with development of familial hypertrophic cardiomyopathy. Hypertrophic cardiomyopathy is usually inherited as an autosomal dominant trait, which mutations reported in cardiac troponin T (TNNT2); myosin heavy chain (MYH7); tropomyosin 1 (TPM1); myosin binding protein C (MYBPC3); 5'-AMP-activated protein kinase subunit gamma-2 (PRKAG2); troponin I type 3 (TNN13); titin (TTN); myosin, light chain 2 (MYL2); actin, alpha cardiac muscle 1 (ACTC1); and cardiac LIM protein (CSRP3).

Arrhythmogenic right ventricular dysplasia (ARVD). ARVD is an autosomal dominant disease of cardiac desmosomes that results in arrhythmia of the right ventricle and sudden cardiac death. It is second only to hypertrophic cardiomyopathy as a leading cause for sudden cardiac death in the young.

Left Ventricular Non-Compaction (LVNC, aka non-compaction cardiomyopathy). LVNC is a hereditary cardiac disease which results from impaired development of the myocardium (heart muscle) during embryogenesis. Patients with mutations causing LVNC develop heart failure and abnormal cardiac electrophysiology early in life.

Double Inlet Left Ventricle (DILV). DILV is a congenital heart defect in which both the left and right atria feed into the left ventricle. As a result, children born with this defect only have one functional ventricular chamber, and trouble pumping oxygenated blood into the general circulation.

Long QT (Type-1) Syndrome (LQT-1, KCNQ1 mutation). Long QT syndrome (LQT) is a hereditary arrhythmic disease in which the QT phase of the electrocardiogram is prolonged, resulting in increased susceptibility for arrhythmia and sudden cardiac death. There are 13 known genes associated with LQT.

By "pluripotency" and pluripotent stem cells it is meant that such cells have the ability to differentiate into all types of cells in an organism. The term "induced pluripotent stem cell" encompasses pluripotent cells, that, like embryonic stem (ES) cells, can be cultured over a long period of time while maintaining the ability to differentiate into all types of cells in an organism, but that, unlike ES cells (which are derived from the inner cell mass of blastocysts), are derived from differentiated somatic cells, that is, cells that had a narrower, more defined potential and that in the absence of experimental manipulation could not give rise to all types of cells in the organism. iPS cells have an hESC-like morphology, growing as flat colonies with large nucleo-cytoplasmic ratios, defined borders and prominent nuclei. In addition, iPS cells express one or more key pluripotency markers known by one of ordinary skill in the art, including but not limited to alkaline phosphatase, SSEA3, SSEA4, Sox2, Oct3/4, Nanog, TRA160, TRA181, TDGF 1, Dnmt3b, FoxD3, GDF3, Cyp26a1, TERT, and zfp42. In addition, the iPS cells are capable of forming teratomas. In addition, they are capable of forming or contributing to ectoderm, mesoderm, or endoderm tissues in a living organism.

As used herein, "reprogramming factors" refers to one or more, i.e. a cocktail, of biologically active factors that act on a cell to alter transcription, thereby reprogramming a cell to multipotency or to pluripotency. Reprogramming factors may be provided to the cells, e.g. cells from an individual with a family history or genetic make-up of interest for heart disease such as fibroblasts, adipocytes, etc.; individually or as a single composition, that is, as a premixed composition, of reprogramming factors. The factors may be provided at the same molar ratio or at different molar ratios. The factors may be provided once or multiple times in the course of culturing the cells of the subject invention. In some embodiments the reprogramming factor is a transcription factor, including without limitation, Oct3/4; Sox2; Klf4; c-Myc; Nanog; and Lin-28.

Somatic cells, including without limitation fibroblasts, adipose derived stem cells, peripheral blood mononuclear cells etc., are contacted with reprogramming factors, as defined above, in a combination and quantity sufficient to reprogram the cell to pluripotency. Reprogramming factors may be provided to the somatic cells individually or as a single composition, that is, as a premixed composition, of reprogramming factors. In some embodiments the reprogramming factors are provided as a plurality of coding sequences on a vector.

Genes may be introduced into the somatic cells or the iPS cells derived therefrom for a variety of purposes, e.g. to replace genes having a loss of function mutation, provide marker genes, etc. Alternatively, vectors are introduced that express antisense mRNA or ribozymes, thereby blocking expression of an undesired gene. Other methods of gene therapy are the introduction of drug resistance genes to enable normal progenitor cells to have an advantage and be subject to selective pressure, for example the multiple drug resistance gene (MDR), or anti-apoptosis genes, such as bcl-2. Various techniques known in the art may be used to introduce nucleic acids into the target cells, e.g. electroporation, calcium precipitated DNA, fusion, transfection, lipofection, infection and the like, as discussed above. The particular manner in which the DNA is introduced is not critical to the practice of the invention.

The iPS cells may also be differentiated into cardiac muscle cells. Inhibition of bone morphogenetic protein (BMP) signaling may result in the generation of cardiac muscle cells (or cardiomyocytes), see, e.g., Yuasa et al., (2005), Nat. Biotechnol., 23(5):607-11. Thus, in an exemplary embodiment, the induced cells are cultured in the presence of noggin for from about two to about six days, e.g., about 2, about 3, about 4, about 5, or about 6 days, prior to allowing formation of an embryoid body, and culturing the embryoid body for from about 1 week to about 4 weeks, e.g., about 1, about 2, about 3, or about 4 weeks.

Cardiomyocyte differentiation may be promoted by including cardiotropic agents in the culture, such as activin A and/or bone morphogenetic protein-4 (see the Examples herein, Xu et al. Regen Med. 2011 Jan;6(1):53-66; Mignone et al. Circ J. 2010 74(12):2517-26; Takei et al. Am J Physiol Heart Circ Physiol. 2009 296(6):H1793-803, each herein specifically incorporated by reference). Examples of such protocols also include, for example, addition of a Wnt agonist, such as Wnt 3A, optionally in the presence of cytokines and growth factors such as BMP4, VEGF and Activin A; followed by culture in the presence of a Wnt antagonist, such a soluble frizzled protein. However, any suitable method of inducing cardiomyocyte differentiation may be used, for example, Cyclosporin A described by Fujiwara et al. PLoS One. 2011 6(2):e16734; Dambrot et al. Biochem J. 2011 434(1):25-35; equiaxial cyclic stretch, angiotensin II, and phenylephrine (PE) described by Foldes et al. J Mol Cell Cardiol. 2011 50(2):367-76; ascorbic acid, dimethylsulfoxide and 5-aza-2'-deoxycytidine described by Wang et al. Sci China Life Sci. 2010 53(5):581-9, endothelial cells described by Chen et al. J Cell Biochem. 2010 111(1):29-39, and the like, which are herein specifically incorporated by reference.

The cells are harvested at an appropriate stage of development, which may be determined based on the expression of markers and phenotypic characteristics of the desired cell type e.g. at from about 1 to 4 weeks. Cultures may be empirically tested by staining for the presence of the markers of interest, by morphological determination, etc. The cells are optionally enriched before or after the positive selection step by drug selection, panning, density gradient centrifugation, etc. In another embodiment, a negative selection is performed, where the selection is based on expression of one or more of markers found on ES cells, fibroblasts, epithelial cells, and the like. Selection may utilize panning methods, magnetic particle selection, particle sorter selection, and the like.

Cardiomyocytes. Phenotypes of cardiomyocytes that arise during development of the mammalian heart can be distinguished: primary cardiomyocytes; nodal cardiomyocytes; conducting cardiomyocytes and working cardiomyocytes. All cardiomyocytes have sarcomeres and a sarcoplasmic reticulum (SR), are coupled by gap junctions, and display automaticity. Cells of the primary heart tube are characterized by high automaticity, low conduction velocity, low contractility, and low SR activity. This phenotype largely persists in nodal cells. In contrast, atrial and ventricular working myocardial cells display virtually no automaticity, are well coupled intercellularly, have well developed sarcomeres, and have a high SR activity. Conducting cells from the atrioventricular bundle, bundle branches and peripheral ventricular conduction system have poorly developed sarcomeres, low SR activity, but are well coupled and display high automaticity.

A "cardiomyocyte precursor" is defined as a cell that is capable of giving rise to progeny that include cardiomyocytes.

Telomeres are repetitive nucleic acid sequences present at the ends of the linear chromosomes of eukaryotic organisms. Telomere sequences, together with telomere-binding proteins, confer stability to chromosomes. Telomeres are generally composed of short tandem repeats with a repeat sequence unit specified by the telomerase enzyme particular to the organism. Telomere repeat sequences are known for a variety of organisms. The human telomere repeat sequence unit is $(TTAGGG)_n$. In addition to the double stranded repeat sequences, the 3' ends of some telomeres contain a single-stranded region, which for humans is located on the G rich strand.

Telomerase is a riboprotein which synthesizes telomeric DNA. In the absence of telomerase, telomeres gradually shorten because DNA polymerases are unable to replicate the ends of linear duplex DNA. The gradual shortening of the telomeres ultimately leads to cell cycle arrest or cell death. In humans, telomere length dependent mortality in cells occurs because of telomerase repression in normal somatic cells before birth, an initial telomere length at birth and throughout life, and tightly regulated expression of telomerase in progenitor or stem cells. Humans are born with "full-length" telomeres. As telomerase is down-regulated in somatic tissues, this leads to loss of telomeric DNA with cellular and chronological age. Thus telomeres act as a mitotic clock, conferring a finite capacity for division on normal human cells. Short telomeres impair the ability of stem cells to proliferate. Telomeres also shorten due to increased ROS in post-mitotic cells such as cardiomyocytes in the absence of proliferation.

A "polynucleotide" or "oligonucleotide" refers to a ribose and/or deoxyribose nucleoside subunit polymer or oligomer having between about 2 and about 200 contiguous subunits. The nucleoside subunits can be joined by a variety of intersubunit linkages, including, but not limited to, phosphodiester, phosphotriester, methylphosphonate, P3'→P5' phosphoramidate, N3'→P5' phosphoramidate, N3→P5' thiophosphoramidate, and phosphorothioate linkages. The term also includes such polymers or oligomers having modifications, known to one skilled in the art, to the sugar (e.g., 2' substitutions), the base (see the definition of "nucleoside," supra), and the 3' and 5' termini. In embodiments where the oligonucleotide moiety includes a plurality of intersubunit linkages, each linkage may be formed using the same chemistry, or a mixture of linkage chemistries may be used. When an oligonucleotide is represented by a sequence of letters, such as "ATGUCCTG," it will be understood that the nucleotides are in 5'→3' order from left to right. Representation of the base sequence of the oligonucleotide in this manner does not imply the use of any particular type of internucleoside subunit in the oligonucleotide.

A "nucleobase" includes (i) native DNA and RNA nucleobases (uracil, thymine, adenine, guanine, and cytosine), (ii) modified nucleobases or nucleobase analogs (e.g., 5-methylcytosine, 5-bromouracil, or inosine) and (iii) nucleobase analogs. A nucleobase analog is a compound whose molecular structure mimics that of a typical DNA or RNA base.

As used herein "telomeric nucleic acids" means a nucleic acid sequence on a double or single stranded nucleic acid which encodes the telomere sequence of the mammal. In humans, the telomeric repeat sequence is TTAGGG on one strand and CCCTAA on the other strand.

An "individual" can be a mammal, such as any common laboratory model organism. Mammals include, but are not limited to, humans and non-human primates, farm animals, sport animals, pets, mice, rats, and other rodents. In some embodiments, an individual is a human.

As used herein, "treatment" (and grammatical variations thereof such as "treat" or "treating") refers to clinical intervention designed to alter the natural course of the individual or cell being treated during the course of clinical pathology. Desirable effects of treatment include, but are not limited to, decreasing the rate of disease progression, amelioration or palliation of the disease state, and remission or improved prognosis.

As used herein, "prevention" includes providing prophylaxis with respect to occurrence or recurrence of a disease or the symptoms associated with a disease in an individual. An individual may be predisposed to, susceptible to, or at risk of developing a disease, but has not yet been diagnosed with the disease.

An "effective amount" or "therapeutically effective amount" refers to an amount of therapeutic compound, such as telomerase enhancing agent, administered to a mammalian subject, either as a single dose or as part of a series of doses, which is effective to produce a desired therapeutic effect.

A "biological sample" is a sample of tissue, blood, lymphatic fluid, etc. obtained from the individual. The biological sample may be a biopsy sample obtained from heart tissue, or a swab of skin cells. The biological sample could include fresh tissue or formalin fixed paraffin embedded tissue or frozen tissue.

As used herein, the singular form "a", "an", and "the" includes plural references unless indicated otherwise.

It is understood that aspects and embodiments of the invention described herein include "comprising," "consisting," and "consisting essentially of" aspects and embodiments.

It is intended that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Methods

In some aspects, methods of the invention comprise the steps of obtaining a sample of cardiomyocyte cell from an individual, where the cells may be obtained from a biopsy sample or from a cell population differentiated in vitro from iPS cells. The average length of telomeres in the cardiomyocyte population is determined. These methods are based on determining the average relative length of telomeres. If the average telomere length in cardiomyocyte cells present in a sample from the individual is determined to be shorter by at least about 10%, at least about 20%, at least about 30%, at least about 40%, at least about 50% or more relative to a matched control, then the individual is diagnosed as susceptible to development of cardiomyopathy, and may be treated in accordance with the diagnosis to mitigate the effects of the disease development. Telomere length is determined by analyzing the length of telomeric nucleotides in cardiomyocyte cells present in a biological sample from the individual.

Biological samples from individuals can be obtained in various ways. For example, a biological sample can be obtained from heart biopsy, or generated in vitro as described above. The biological sample may be obtained by any method known in the art including, but not limited to, needle or core biopsy or fine needle aspiration. Additionally, the biological sample may be fixed, paraffin embedded, fresh, or frozen before telomere length is determined.

Numerous methods are available in the art for determining telomere length from cells in biological samples according to the methods disclosed herein.

In one aspect, telomere length can be determined by measuring the mean length of a terminal restriction fragment (TRF). The TRF is defined as the length-in general the average length-of fragments resulting from complete digestion of genomic DNA with a restriction enzyme that does not cleave the nucleic acid within the telomeric sequence. Typically, the DNA is digested with restriction enzymes that cleaves frequently within genomic DNA but does not cleave within telomere sequences. Typically, the restriction enzymes have a four base recognition sequence (e.g., AluI, HinfI, RsaI, and Sau3A1) and are used either alone or in combination. The resulting terminal restriction fragment contains both telomeric repeats and subtelomeric DNA. As used herein, subtelomeric DNA are DNA sequences adjacent to tandem repeats of telomeric sequences and contain telomere repeat sequences interspersed with variable telomeric-like sequences. The digested DNA is separated by electrophoresis and blotted onto a support, such as a membrane. The fragments containing telomere sequences are detected by hybridizing a probe, i.e., labeled repeat sequences, to the membrane. Upon visualization of the telomere containing fragments, the mean lengths of terminal restriction fragments can be calculated (Harley, C. B. et al., Nature. 345(6274):458-60 (1990), hereby incorporated by reference). TRF estimation by Southern blotting gives a distribution of telomere length in the cells or tissue, and thus the mean telomere length of all cells.

For the various methods described herein, a variety of hybridization conditions may be used, including high, moderate, and low stringency conditions (see, e.g., Sambrook, J. Molecular Cloning: A Laboratory Manual, 3rd Ed., Cold Spring Harbor Laboratory Press, Cold Spring Harbor, N.Y. (2001); Ausubel, F. M. et al., Current Protocols in Molecular Biology, John Wiley & Sons (updates to 2002); hereby incorporated by reference).

In another aspect, telomere lengths can be measured by flow cytometry (Hultdin, M. et al., Nucleic Acids Res. 26: 3651-3656 (1998); Rufer, N. et al., Nat. Biotechnol. 16:743-747 (1998); incorporated herein by reference). Flow cytometry methods are variations of FISH techniques. If the starting material is tissue, a cell suspension is made, generally by mechanical separation and/or treatment with proteases. Cells are fixed with a fixative and hybridized with a telomere sequence specific probe, preferably a PNA probe, labeled with a fluorescent label. Following hybridization, cell are washed and then analyzed by FACS. Fluorescence signal is measured for cells in Go/GI following appropriate subtraction for background fluorescence. This technique is suitable for rapid estimation of telomere length for large numbers of samples. Similar to TRF, telomere length is the average length of telomeres within the cell.

In other aspects, the average length of telomeres from cells within a biological sample is determined via quantitative PCR (qPCR) or telomere fluorescent in situ hybridization (telo-FISH).

In some aspects, telomere length is determined using qPCR from DNA extracted from formalin fixed, paraffin embedded (FFPE) biological samples. In qPCR, a DNA binding dye binds to all double-stranded DNA causing fluorescence of the dye. An increase in DNA product during the PCR reaction leads to an increase in the fluorescence intensity and is measured at each cycle of the PCR reaction. This allows the DNA concentration to be quantified. The relative concentration of the DNA present during the exponential phase of the reaction is determined by plotting the level of fluorescence against the PCR cycle number on a semi-logarithmic scale. A threshold for detection of fluorescence above background is determined. The cycle at which the fluorescence from the sample crosses the threshold is called the cycle threshold (Ct). Because the quantity of DNA theoretically doubles every cycle during the exponential phase, the relative amounts of DNA can be calculated. The baseline is the initial cycles of PCR, in which there is little change in fluorescence signal.

Telomeric nucleic acids can be extracted from formalin fixed, paraffin embedded biological samples using a mild extraction method. For instance the sample may be treated using detergents, sonication, electroporation, denaturants, etc. to disrupt the cells. The target nucleic acids may be purified as needed. It has been found that mild extraction methods which do not use a column to isolate the nucleic acids are beneficial because these methods retain the smaller fragments of nucleic acid in the final nucleic acid preparation (small DNA fragments are found in FFPE samples and can be lost during column extraction). In some embodiments, the extraction methods retain a majority of the telomeric target nucleic acid fragments that are at least 50 bp, at least 60 bp, at least 70 bp, at least 80 bp. In one embodiment, the FFPE sample can be deparaffinated prior to extraction of the DNA. In another embodiment, the DNA can be extracted from the FFPE sample without prior deparaffination of the FFPE sample. Following DNA extraction, the DNA is labeled with a fluorescent dye (such as SYBR Green I, Invitrogen, Carlsbad, Calif.). Following DNA labeling, a polymerase chain reaction is performed using a target single copy nucleic acid extracted from the formalin-fixed paraffin biological sample (comprising substantially complementary first and second strands), a first single copy gene primer (wherein the first single copy gene primer is capable of (i) hybridizing to the first strand of the target single copy gene nucleic acid and (ii) being extended by DNA polymerase to form an extended single copy gene primer), and a second single copy gene primer (wherein the second single copy gene primer is capable of (i) hybridizing to the extended first single copy gene primer and/or the target DNA and (ii) being extended by DNA polymerase), and allowing the polymerase chain reaction to proceed in cycles of denaturation and extension and identifying the replication cycle at which the threshold PCR signal is passed.

Telomere length may be expressed as the telomere product normalized by single copy gene product. In other words, relative telomere length of a sample is the factor by which the experimental sample differs from a reference DNA sample in its ratio of telomere repeat copy number to single gene copy number. The quantity of telomere repeats in each experimental sample is measured as the level of dilution of an arbitrarily chosen reference DNA sample that would make the experimental and reference samples equivalent with regard to the number of cycles of PCR needed to generate a given amount of telomere PCR product during the exponential phase of PCR amplification. Similarly the relative quantity of the single copy gene in each experimental sample is expressed as the level of dilution of the reference DNA sample needed to match it to the experimental sample with regard to the number of cycles of PCR needed to generate a given amount of single copy gene PCR product during the exponential phase of the PCR.

Correlation of the measured telomere length of the individual and the population is examined by various statistical methods, such as survival analysis, including Cox proportional hazard regression models, Kaplan-Meier survival distribution estimate, Peto Wilcoxon test, maximum likelihood analysis, multiple regression analysis and others.

In some aspects, telomere length is determined using telo-FISH. In this method, cells are fixed and hybridized with a probe conjugated to a fluorescent label, for example, Cy-3, fluoresceine, rhodamine, etc. Probes for this method are oligonucleotides designed to hybridize specifically to telomere sequences. Generally, the probes are 8 or more nucleotides in length, such as 12-20 or more nucleotides in length. In one aspect, the probes are oligonucleotides comprising naturally occurring nucleotides. In one aspect, the probe is a peptide nucleic acid, which has a higher $T_m$ than analogous natural sequences, and thus permits use of more stringent hybridization conditions. Cells may be treated with an agent, such as colcemid, to induce cell cycle arrest at metaphase provide metaphase chromosomes for hybridization and analysis. In some embodiments, cellular DNA can also be stained with the fluorescent dye 4',6-diamidino-2-phenylindole (DAPI).

Digital images of intact metaphase chromosomes are acquired and the fluorescence intensity of probes hybridized to telomeres quantitated. This permits measurement of telomere length of individual chromosomes, in addition to average telomere length in a cell, and avoids problems associated with the presence of subtelomeric DNA (Zjilmans, J. M. et al., Proc. Natl. Acad Sci. USA 94:7423-7428 (1997); Blasco, M. A. et al., Cell 91:25-34 (1997); incorporated by reference). The intensity of the fluorescent signal correlates with the length of the telomere, with a brighter fluorescent signal indicating a longer telomere.

In some aspects, software is utilized to quantitate the average telomere length from cells obtained from biological samples and subjected to telo-FISH. In one embodiment, the software is used to draw one or more lines around (i) the cells' nuclei, which is determined based on the location of the DAPI stain, and (ii) around the telomeres. Once each nucleus and telomere is encircled, the software can calculate the intensity of each individual telomere in the cells and thereby determine the average telomere length for the cells derived from the biological sample.

Screening Methods

The methods of the invention include screening compounds that mimic or increase activity of telomerase. Alternative screening may determine activity in interfering with telomere-p53-mitochondria-ROS signaling. Such screening methods may include, for example, a step of determining activity in a biological setting, e.g. increasing telomere length. A wide variety of assays may be used for this purpose, including labeled in vitro protein-protein binding assays, electrophoretic mobility shift assays, immunoassays for protein binding, and the like. Knowledge of the 3-dimensional structure leads to the rational design of small drugs that specifically mimic their activity.

Candidate agents of interest are biologically active agents that encompass numerous chemical classes, primarily organic molecules, which may include organometallic molecules, inorganic molecules, genetic sequences, etc. An important aspect of the invention is to evaluate candidate drugs, select therapeutic antibodies and protein-based therapeutics, with preferred biological response functions. Candidate agents comprise functional groups necessary for structural interaction with proteins, particularly hydrogen bonding, and typically include at least an amine, carbonyl, hydroxyl or carboxyl group, frequently at least two of the functional chemical groups. The candidate agents often comprise cyclical carbon or heterocyclic structures and/or aromatic or polyaromatic structures substituted with one or more of the above functional groups. Candidate agents are also found among biomolecules, including peptides, polynucleotides, saccharides, fatty acids, steroids, purines, pyrimidines, derivatives, structural analogs or combinations thereof.

Included are pharmacologically active drugs, genetically active molecules, etc. Compounds of interest include chemotherapeutic agents, anti-inflammatory agents, hormones or hormone antagonists, ion channel modifiers, and neuroactive agents. Exemplary of pharmaceutical agents suitable for this invention are those described in, "The Pharmacological Basis of Therapeutics," Goodman and Gilman, McGraw-Hill, New York, N.Y., (1996), Ninth edition, under the sections: Drugs Acting at Synaptic and Neuroeffector Junctional Sites; Drugs Acting on the Central Nervous System; Autacoids: Drug Therapy of Inflammation; Water, Salts and Ions; Drugs Affecting Renal Function and Electrolyte Metabolism; Cardiovascular Drugs; Drugs Affecting Gastrointestinal Function; Drugs Affecting Uterine Motility; Chemotherapy of Parasitic Infections; Chemotherapy of Microbial Diseases; Chemotherapy of Neoplastic Diseases; Drugs Used for Immunosuppression; Drugs Acting on Blood-Forming organs; Hormones and Hormone Antagonists; Vitamins, Dermatology; and Toxicology, all incorporated herein by reference.

Test compounds include all of the classes of molecules described above, and may further comprise samples of unknown content. Of interest are complex mixtures of naturally occurring compounds derived from natural sources such as plants. While many samples will comprise compounds in solution, solid samples that can be dissolved in a suitable solvent may also be assayed. Samples of interest include environmental samples, e.g. ground water, sea water, mining waste, etc.; biological samples, e.g. lysates prepared from crops, tissue samples, etc.; manufacturing samples, e.g. time course during preparation of pharmaceuticals; as well as libraries of compounds prepared for analysis; and the like. Samples of interest include compounds being assessed for potential therapeutic value, i.e. drug candidates.

The term samples also includes the fluids described above to which additional components have been added, for example components that affect the ionic strength, pH, total protein concentration, etc. In addition, the samples may be treated to achieve at least partial fractionation or concentration. Biological samples may be stored if care is taken to reduce degradation of the compound, e.g. under nitrogen, frozen, or a combination thereof. The volume of sample used is sufficient to allow for measurable detection, usually from about 0.1 µl to 1 ml of a biological sample is sufficient.

Compounds, including candidate agents, are obtained from a wide variety of sources including libraries of synthetic or natural compounds. For example, numerous means are available for random and directed synthesis of a wide variety of organic compounds, including biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Agents are screened for biological activity by adding the agent to at least one and usually a plurality of assay conditions, for example in conjunction with assay conditions where the agent is not present, conditions where a known activator are present, conditions in which a known activity is expected, e.g. cyclic AMP release, and the like. The change in parameter readout in response to the agent is measured, desirably normalized, and the resulting data may then be evaluated by comparison to reference data.

The agents are conveniently added in solution, or readily soluble form, to the medium of cells in culture. The agents may be added in a flow-through system, as a stream, intermittent or continuous, or alternatively, adding a bolus of the compound, singly or incrementally, to an otherwise static solution. In a flow-through system, two fluids are used, where one is a physiologically neutral solution, and the other is the same solution with the test compound added. The first fluid is passed over the cells, followed by the second. In a single solution method, a bolus of the test compound is added to the volume of medium surrounding the cells. The overall concentrations of the components of the culture medium should not change significantly with the addition of the bolus, or between the two solutions in a flow through method.

Preferred agent formulations do not include additional components, such as preservatives, that may have a significant effect on the overall formulation. Thus preferred formulations consist essentially of a biologically active compound and a physiologically acceptable carrier, e.g. water, ethanol, DMSO, etc. However, if a compound is liquid without a solvent, the formulation may consist essentially of the compound itself.

A plurality of assays may be run in parallel with different agent concentrations to obtain a differential response to the various concentrations. As known in the art, determining the effective concentration of an agent typically uses a range of concentrations resulting from 1:10, or other log scale, dilutions. The concentrations may be further refined with a second series of dilutions, if necessary. Typically, one of these concentrations serves as a negative control, i.e. at zero concentration or below the level of detection of the agent or at or below the concentration of agent that does not give a detectable change in the phenotype.

The compounds having the desired pharmacological activity may be administered in a physiologically acceptable carrier to a host for modulation of breathing, etc. The agents may be administered in a variety of ways, orally, by inhalation, topically, parenterally e.g. subcutaneously, intraperitoneally, by viral infection, intravascularly, etc. Depending upon the manner of introduction, the compounds may be formulated in a variety of ways. The concentration of therapeutically active compound in the formulation may vary from about 0.1-10 wt %.

Binding assays may be performed conventionally. Biological assays, e.g. detection of a sigh signature in an in vitro brain slice, may be generated from a biological sample using any convenient protocol, for example as described in the examples. The readout may be a mean, average, median or the variance or other statistically or mathematically-derived value associated with the measurement. A signature pattern may be evaluated on a number of points: to determine if there is a statistically significant change at any point in the data matrix; whether the change is an increase or decrease in the motor neuron output; whether the change is specific for one or more physiological states or factors, and the like.

Following obtainment of the signature pattern from the sample being assayed, the signature pattern is compared with a reference or control profile to make an evaluation regarding activity of a candidate agent, and the like. Typically a comparison is made with a sample or set of samples from a control profile.

In order to identify profiles that are indicative of responsiveness, a statistical test will provide a confidence level for a change in the expression, titers or concentration of markers between the test and control profiles to be considered significant, where the control profile may be for responsiveness or non-responsiveness. The raw data may be initially analyzed by measuring the values for each marker, usually in duplicate, triplicate, quadruplicate or in 5-10 replicate features per marker.

The analysis and database storage may be implemented in hardware or software, or a combination of both. In one embodiment of the invention, a machine-readable storage medium is provided, the medium comprising a data storage material encoded with machine readable data which, when using a machine programmed with instructions for using said data, is capable of displaying a any of the datasets and data comparisons of this invention. Such data may be used for a variety of purposes, such as patient monitoring, initial diagnosis, and the like. Preferably, the invention is implemented in computer programs executing on programmable computers, comprising a processor, a data storage system (including volatile and non-volatile memory and/or storage elements), at least one input device, and at least one output device. Program code is applied to input data to perform the functions described above and generate output information. The output information is applied to one or more output devices, in known fashion. The computer may be, for example, a personal computer, microcomputer, or workstation of conventional design.

Each program is preferably implemented in a high level procedural or object oriented programming language to communicate with a computer system. However, the programs can be implemented in assembly or machine language, if desired. In any case, the language may be a compiled or interpreted language. Each such computer program is preferably stored on a storage media or device (e.g., ROM or magnetic diskette) readable by a general or special purpose programmable computer, for configuring and operating the computer when the storage media or device is read by the computer to perform the procedures described herein. The system may also be considered to be implemented as a computer-readable storage medium, configured with a computer program, where the storage medium so configured causes a computer to operate in a specific and predefined manner to perform the functions described herein.

A variety of structural formats for the input and output means can be used to input and output the information in the computer-based systems of the present invention. One format for an output means test datasets possessing varying degrees of similarity to a trusted profile. Such presentation provides a skilled artisan with a ranking of similarities and identifies the degree of similarity contained in the test pattern.

The signature patterns and databases thereof may be provided in a variety of media to facilitate their use. "Media" refers to a manufacture that contains the signature pattern information of the present invention. The databases of the present invention can be recorded on computer readable media, e.g. any medium that can be read and accessed directly by a computer. Such media include, but are not limited to: magnetic storage media, such as floppy discs, hard disc storage medium, and magnetic tape; optical storage media such as CD-ROM; electrical storage media such as RAM and ROM; and hybrids of these categories such as magnetic/optical storage media. One of skill in the art can readily appreciate how any of the presently known computer readable mediums can be used to create a manufacture comprising a recording of the present database information. "Recorded" refers to a process for storing information on computer readable medium, using any such methods as known in the art. Any convenient data storage structure may be chosen, based on the means used to access the stored information. A variety of data processor programs and formats can be used for storage, e.g. word processing text file, database format, etc.

As used herein "active compounds" in addition to their free base and quaternized forms also encompasses pharmaceutically acceptable, pharmacologically active derivatives of active compounds including individual enantiomers and their pharmaceutically acceptable salts, mixtures of enantiomers and their pharmaceutically acceptable salts, and active metabolites of active compounds and their pharmaceutically acceptable salts, unless otherwise noted. It is understood that in some cases dosages of enantiomers, derivatives, and metabolites may need to be adjusted based on relative activity of the racemic mixture of active compound.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxyrnaleic, phenylacetic, glutamic, benzoic, salicylic, sulfanilic, 2-acetoxybenzoic, fumaric, toluenesulfonic, methanesulfonic, ethane disulfonic, oxalic, and isethionic.

The pharmaceutically acceptable salts of the compounds can be synthesized from the parent compound, which contains a basic or acidic moiety, by conventional chemical methods.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio.

As used herein, the term "stereoisomers" refers to compounds made up of the same atoms bonded by the same bonds but having different spatial structures which are not interchangeable. The three-dimensional structures are called configurations. As used herein, the term "enantiomers" refers to two stereoisomers whose molecules are nonsuperimposable mirror images of one another. As used herein, the term "optical isomer" is equivalent to the term "enantiomer". The terms "racemate", "racemic mixture" or "racemic modification" refer to a mixture of equal parts of enantiomers. The term "chiral center" refers to a carbon atom to which four different groups are attached. The term "enantiomeric enrichment" as used herein refers to the increase in the amount of one enantiomer as compared to the other. Enantiomeric enrichment is readily determined by one of ordinary skill in the art using standard techniques and procedures, such as gas or high performance liquid chromatography with a chiral column. Choice of the appropriate chiral column, eluent and conditions necessary to effect separation of the enantiomeric pair is well within the knowledge of one of ordinary skill in the art using standard techniques well known in the art, such as those described by J. Jacques, et al., "Enantiomers, Racemates, and Resolutions", John Wiley and Sons, Inc., 1981. Examples of resolutions include recrystallization of diastereomeric salts/derivatives or preparative chiral chromatography.

By adjunctive administration is meant simultaneous administration of the compounds, in the same dosage form, simultaneous administration in separate dosage forms, and separate administration of the compounds.

Formulations are prepared using a pharmaceutically acceptable "carrier" composed of materials that are considered safe and effective and may be administered to an individual without causing undesirable biological side effects or unwanted interactions. The "carrier" is all components present in the pharmaceutical formulation other than the active ingredient or ingredients. The term "carrier" includes but is not limited to diluents, binders, lubricants, disintegrators, fillers, and coating compositions.

"Carrier" also includes all components of the coating composition which may include plasticizers, pigments, colorants, stabilizing agents, and glidants. The delayed release dosage formulations may be prepared as described in references such as "Pharmaceutical dosage form tablets", eds. Liberman et. al. (New York, Marcel Dekker, Inc., 1989), "Remington-The science and practice of pharmacy", 20th ed., Lippincott Williams & Wilkins, Baltimore, Md., 2000, and "Pharmaceutical dosage forms and drug delivery systems", .sup.6th Edition, Ansel et. al., (Media, Pa.: Williams and Wilkins, 1995) which provides information on carriers, materials, equipment and process for preparing tablets and capsules and delayed release dosage forms of tablets, capsules, and granules.

Examples of suitable coating materials include, but are not limited to, cellulose polymers such as cellulose acetate phthalate, hydroxypropyl cellulose, hydroxypropyl methylcellulose, hydroxypropyl methylcellulose phthalate and hydroxypropyl methylcellulose acetate succinate; polyvinyl acetate phthalate, acrylic acid polymers and copolymers, and methacrylic resins that are commercially available under the trade name Eudragit.®. (Roth Pharma, Westerstadt, Germany), Zein, shellac, and polysaccharides.

Additionally, the coating material may contain conventional carriers such as plasticizers, pigments, colorants, glidants, stabilization agents, pore formers and surfactants.

Optional pharmaceutically acceptable excipients present in the drug-containing tablets, beads, granules or particles include, but are not limited to, diluents, binders, lubricants, disintegrants, colorants, stabilizers, and surfactants. Diluents, also termed "fillers," are typically necessary to increase the bulk of a solid dosage form so that a practical size is provided for compression of tablets or formation of beads and granules. Suitable diluents include, but are not limited to, dicalcium phosphate dihydrate, calcium sulfate, lactose, sucrose, mannitol, sorbitol, cellulose, microcrystalline cellulose, kaolin, sodium chloride, dry starch, hydrolyzed starches, pregelatinized starch, silicone dioxide, titanium oxide, magnesium aluminum silicate and powder sugar.

Binders are used to impart cohesive qualities to a solid dosage formulation, and thus ensure that a tablet or bead or granule remains intact after the formation of the dosage forms. Suitable binder materials include, but are not limited to, starch, pregelatinized starch, gelatin, sugars (including sucrose, glucose, dextrose, lactose and sorbitol), polyethylene glycol, waxes, natural and synthetic gums such as acacia, tragacanth, sodium alginate, cellulose, including hydroxypropylmethylcellulose, hydroxypropylcellulose, ethylcellulose, and veegum, and synthetic polymers such as acrylic acid and methacrylic acid copolymers, methacrylic acid copolymers, methyl methacrylate copolymers, aminoalkyl methacrylate copolymers, polyacrylic acid/polymethacrylic acid and polyvinylpyrrolidone.

Lubricants are used to facilitate tablet manufacture. Examples of suitable lubricants include, but are not limited to, magnesium stearate, calcium stearate, stearic acid, glycerol behenate, polyethylene glycol, talc, and mineral oil.

Disintegrants are used to facilitate dosage form disintegration or "breakup" after administration, and generally include, but are not limited to, starch, sodium starch glycolate, sodium carboxymethyl starch, sodium carboxymethylcellulose, hydroxypropyl cellulose, pregelatinized starch, clays, cellulose, alginine, gums or cross linked polymers, such as cross-linked PVP (Polyplasdone XL from GAF Chemical Corp).

Stabilizers are used to inhibit or retard drug decomposition reactions which include, by way of example, oxidative reactions.

Surfactants may be anionic, cationic, amphoteric or nonionic surface active agents. Suitable anionic surfactants include, but are not limited to, those containing carboxylate, sulfonate and sulfate ions. Examples of anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine. Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamer.®. 401, stearoyl monoisopropanolamide, and polyoxyethylene hydrogenated tallow amide. Examples of amphoteric surfactants include sodium N-dodecyl-.beta.-alanine, sodium N-lauryl-.beta.-iminodipropionate, myristoamphoacetate, lauryl betaine and lauryl sulfobetaine.

If desired, the tablets, beads granules or particles may also contain minor amount of nontoxic auxiliary substances such as wetting or emulsifying agents, dyes, pH buffering agents, and preservatives.

The immediate release dosage unit of the dosage form-i.e., a tablet, a plurality of drug-containing beads, granules or particles, or an outer layer of a coated core dosage form-contains a therapeutically effective quantity of the active agent with conventional pharmaceutical excipients. The immediate release dosage unit may or may not be coated, and may or may not be admixed with the delayed release dosage unit or units (as in an encapsulated mixture of immediate release drug-containing granules, particles or beads and delayed release drug-containing granules or beads).

Each dosage form contains a therapeutically effective amount of active agent. The effective dose may be from about 0.1 µg to about 1 g/kg weight of the subject. For dosage forms that mimic the twice daily dosing profile, approximately 30 wt. % to 80 wt. %, preferably 40 wt. % to 70 wt. %, of the total amount of active agent in the dosage form is released in the initial pulse, and, correspondingly approximately 70 wt. % to 20 wt. %, preferably 60 wt. % to 30 wt. %, of the total amount of active agent in the dosage form is released in the second pulse. For dosage forms mimicking the twice daily dosing profile, the second pulse is preferably released approximately 3 hours to less than 14 hours, and most preferably approximately 5 hours to 12 hours, following administration.

A kit is provided wherein the pharmaceutical composition of the invention is packaged accompanied by instructions. The packaging material may be a box, bottle, blister package, tray, or card. The kit will include a package insert instructing the patient to take a specific dose at a specific time, for example, a first dose on day one, a second dose on day two, a third dose on day three, and so on, until a maintenance dose is reached.

As will be appreciated by those skilled in the art and as described in the pertinent texts and literature, a number of methods are available for preparing drug-containing tablets, beads, granules or particles that provide a variety of drug release profiles. Such methods include, but are not limited to, the following: coating a drug or drug-containing composition with an appropriate coating material.

The methods illustrated in this disclosure are not intended to be exclusive of other methods within the scope of the present subject matter. Those of ordinary skill in the art will understand, upon reading and comprehending this disclosure, other methods within the scope of the present subject matter. The above-identified embodiments, and portions of the illustrated embodiments, are not necessarily mutually exclusive. These embodiments, or portions thereof, can be combined. In various embodiments, the methods provided above are implemented as a computer data signal embodied in a carrier wave or propagated signal, that represents a sequence of instructions which, when executed by a processor cause the processor to perform the respective method. In various embodiments, methods provided above are implemented as a set of instructions contained on a computer-accessible medium capable of directing a processor to perform the respective method. In various embodiments, the medium is a magnetic medium, an electronic medium, or an optical medium.

Although specific embodiments have been illustrated and described herein, it will be appreciated by those of ordinary skill in the art that any arrangement which is calculated to achieve the same purpose may be substituted for the specific embodiment shown. This application is intended to cover adaptations or variations of the present subject matter. It is to be understood that the above description is intended to be illustrative, and not restrictive. Combinations of the above embodiments as well as combinations of portions of the above embodiments in other embodiments will be apparent to those of skill in the art upon reviewing the above description. The scope of the present subject matter should be determined with reference to the appended claims, along with the full scope of equivalents to which such claims are entitled.

EXPERIMENTAL

Telomere Length as a Novel Biomarker in Sarcomeric Dilated Cardiomyopathy.

Dilated Cardiomyopathy (DCM) is a cardiac disease characterized by dilatation of the ventricular chamber resulting in decreased systolic contractile function. DCM mostly occurs between the ages of 20 to 60 reportedly affecting approximately 1 in 2500 although this is likely an underestimate of the incidence. DCM is the most common cause of heart failure after coronary artery disease and hypertension, as well as the leading indication for heart transplantations. It is estimated that genetic mutations accounts for 20-40% of the DCM cases and are termed familial DCM; the remaining 60-80% are "idiopathic"—either familial or sporadic—or unknown. Molecularly, DCM has been described to exhibit abnormal mechanical linkage of the extracellular matrix to the cytoskeleton, disarrangement of Z-disc proteins, decreased myofilament calcium sensitivity, ion channel abnormalities, and remodeled intracellular calcium handling. However, the heterogeneous etiologies underlying DCM also have limited our understanding of the pathogenesis of DCM and better biomarkers are warranted.

Telomeres are DNA-protein complexes that are located at the ends of chromosomes and by replication insufficiency, the length of telomeric repeats shorten every cell division. In Duchenne Muscular Dystrophy (DMD) DCM, telomere shortening occurred specifically in cardiomyocytes in both patient cardiac samples and in a novel mouse model (mdx/mTRK$^{KO}$, lacking dystrophin and with shortened telomeres that manifests DCM). In healthy cardiomyocytes, telomere lengths are maintained throughout life; moreover, the low frequency of cardiomyocyte proliferation observed by $^{13}$C labeling suggests that the shortened telomeres in DMD correspond to accelerated aging due to dystrophin-deficiency.

Troponin T2 (TNNT2) DCM is characterized by a point mutation in exon 12 (R173W). Telomere length was measured in both patient cardiac samples as well as in cardiomyocytes derived from patient induced pluripotent stem cell (iPSC-CM).

Figure 1A:
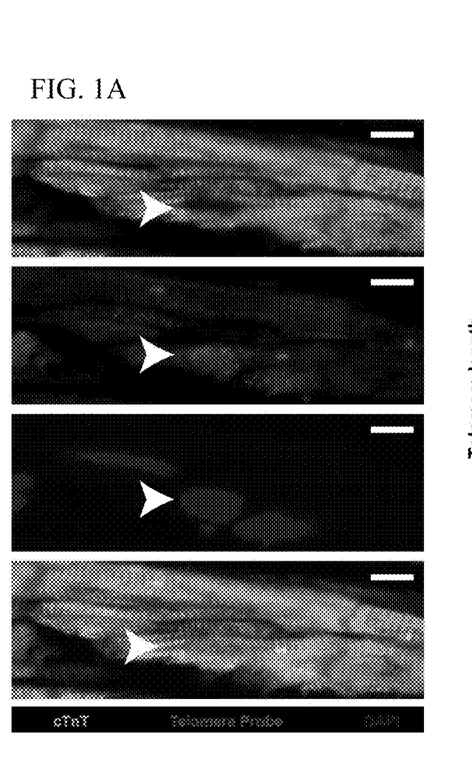
(FIG. 1A) Telomere length (TeIC) was evaluated by immunofluorescence staining relative to DAPI staining in cardiac troponin T positive cardiomyocytes in patient cardiac sections.
Figure 1B:
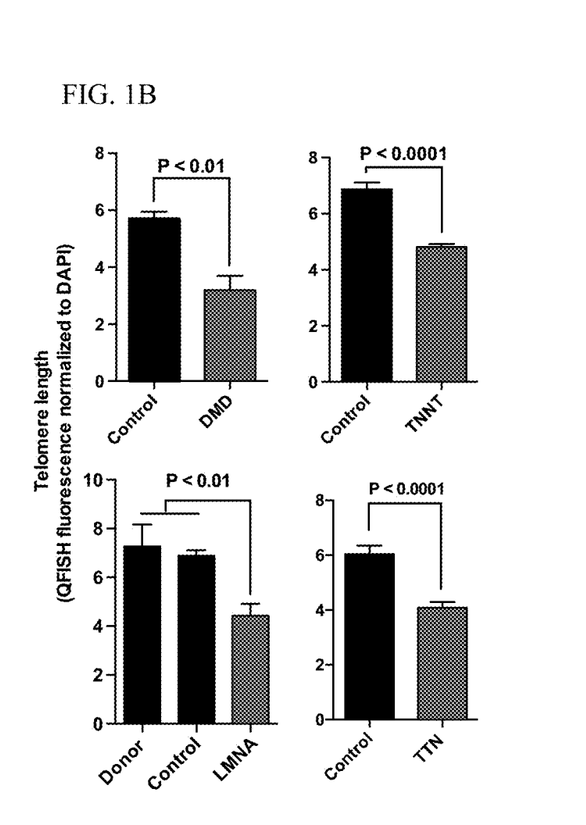
Figure 2A:
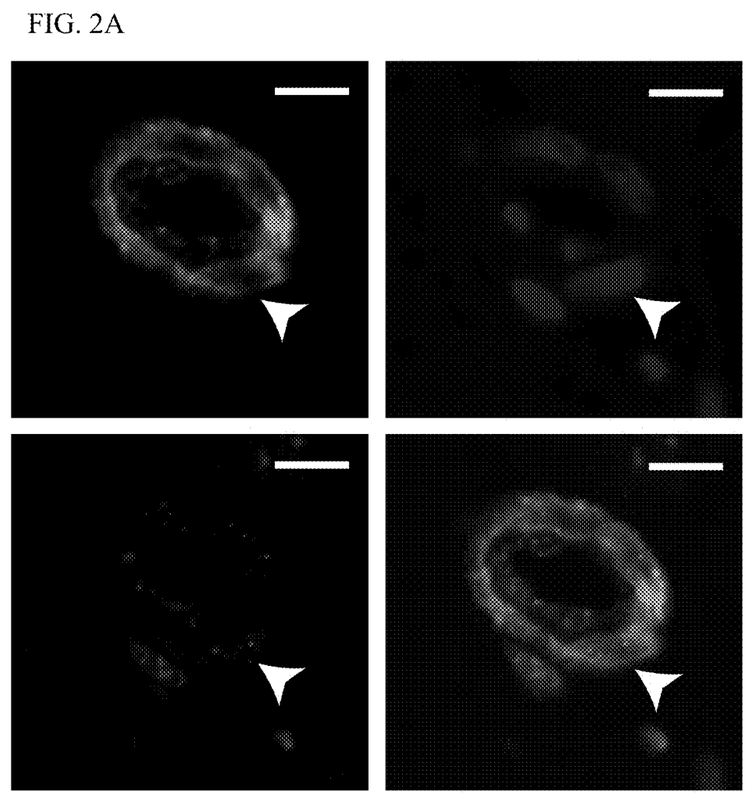
Figure 2B:
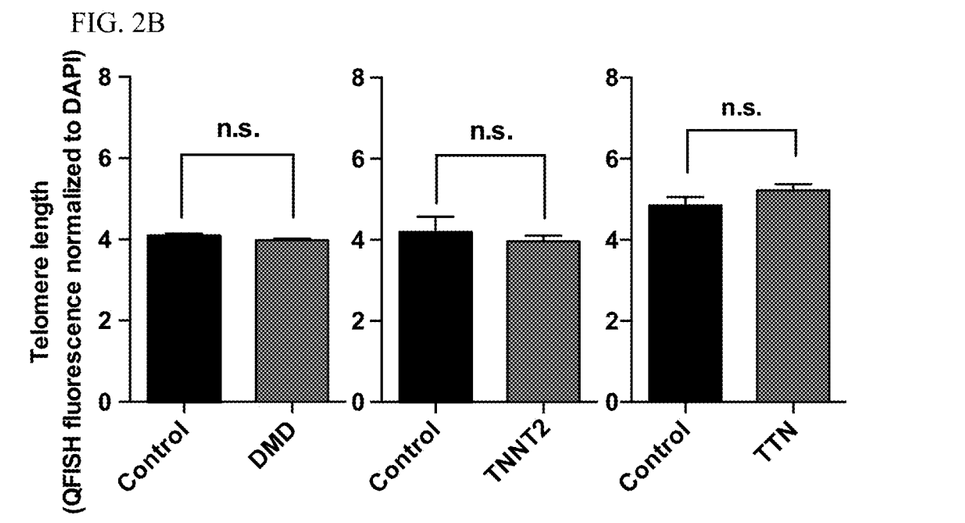

Using quantitative in situ hybridization (QFISH), we first measured relative telomere length using a PNA probe against the telomere repeat sequence (TTAGGG) in primary patient cardiac samples (FIG. 1a). Compared to healthy age and gender-matched controls, dystrophin (DMD), troponin T2 (TNNT2), lamin A (LMNA) and titin (TTN) cardiomyocytes all exhibited a significant decrease in telomere length (FIG. 1b; ~30-50%). Importantly, vascular smooth muscle cells that do not require the expression of DMD, TNNT2 nor TTN showed no alterations in telomere length suggesting that the telomere shortening observed is driven by sarcomere deficiency (FIG. 2). These data demonstrate that telomere shortening, which could be viewed as accelerated aging, occurs in contractile cells (cardiomyocytes) that require the expression of sarcomeric genes (dystrophin, troponin T2, and titin) but not in non-contractile cells (vascular smooth muscle cells).

Figure 3A:
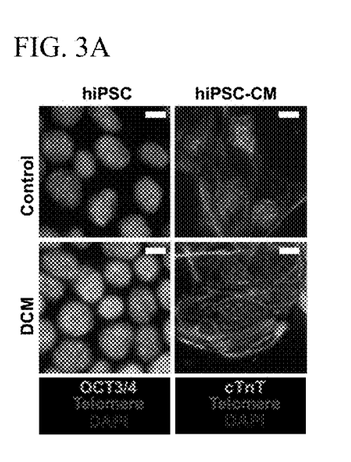
Figure 3B:
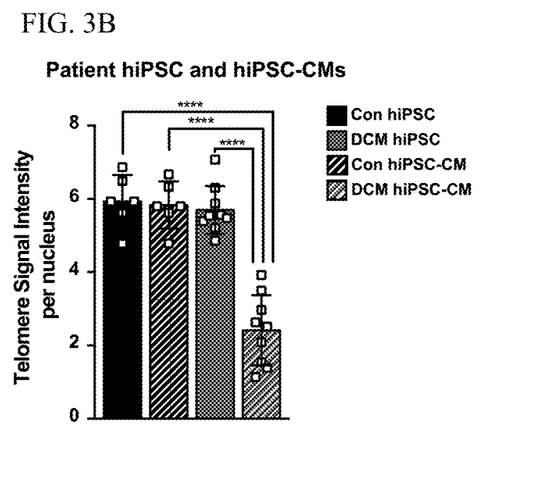
Figure 3C:
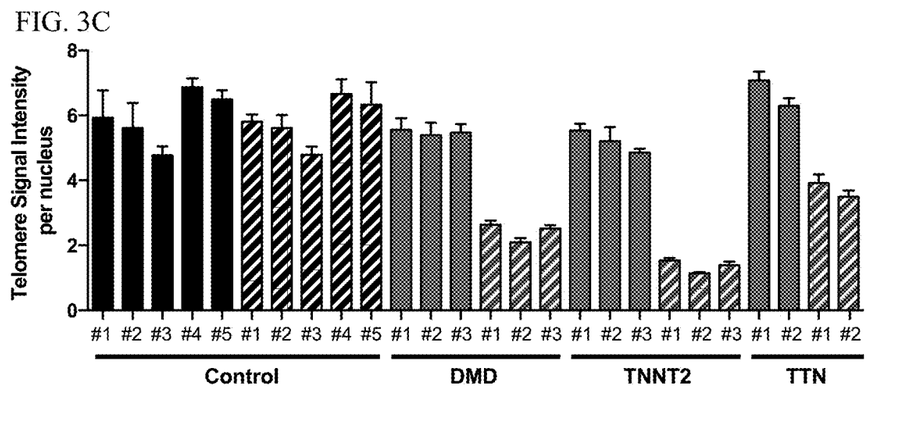

Using the induced pluripotent stem cells (iPSCs) platform, functional cardiomyocytes can be obtained from DCM patients by differentiation of human iPSCs. DMD and LMNA iPSC lines were generated at Stanford; TNNT2 and TTN iPSC lines were established from previous work. All iPSC-CMs were derived using the existing differentiation protocol. Importantly, to ensure the basal telomere length was comparable between the different iPSC lines for mutations that do not affect non-contracting iPSCs (DMD and TNNT2), we measured telomere lengths in both the starting iPSC as well as iPSC-CMs after 30 days of differentiation (FIG. 3a). Prior to differentiation, there is no significant difference in basal telomere length between the iPSC lines (FIGS. 3b&c). However, compared to iPSC-CMs from healthy controls or CRISPR/Cas9-corrected isogenic controls, DMD, TNNT2 and LMNA iPSC-CMs displayed a significant decrease in telomere length (FIGS. 2b).

Figure 4A:
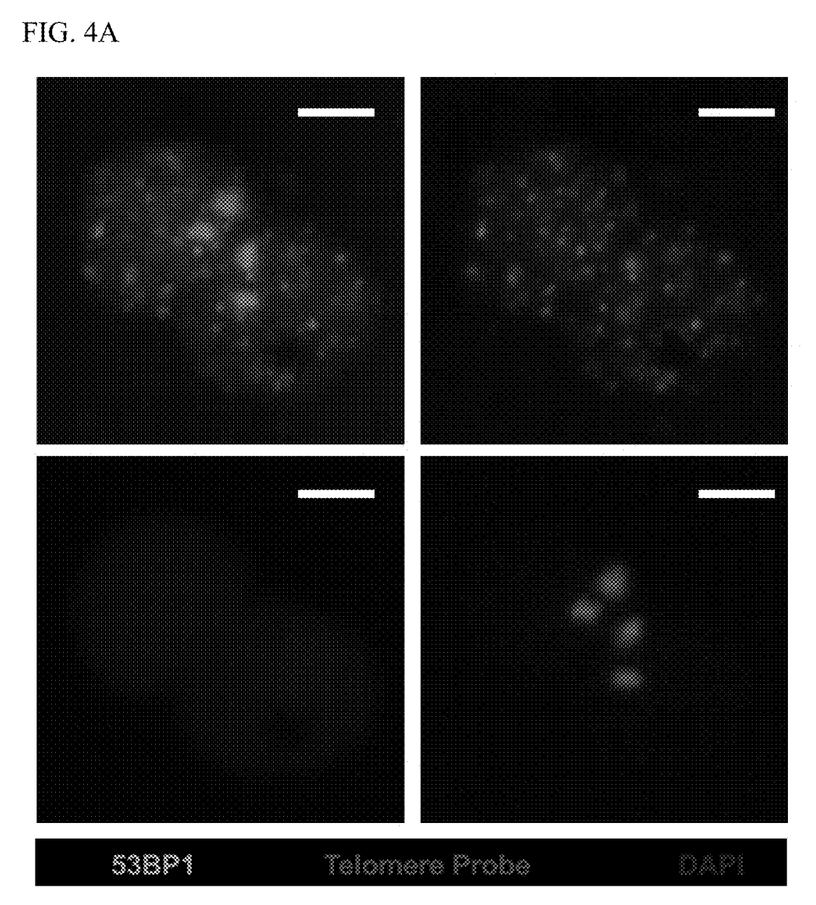
Figure 4B:
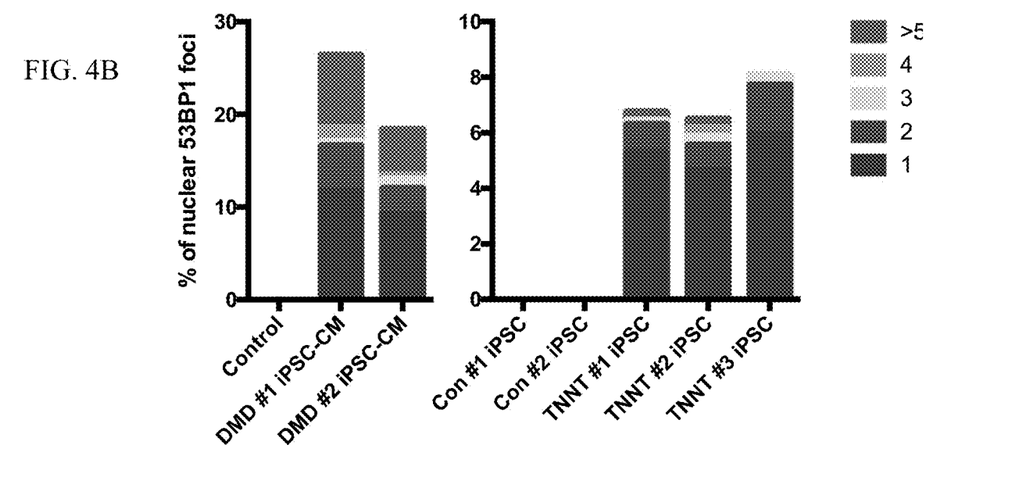

Critically shortened telomeres have been shown to be capable of inducing DNA damage response. Using p53 binding protein 1 (53BP1) as a marker for DNA damage response, we observed a significant increase in percentage of total iPSC-CMs exhibiting nuclear 53BP1 foci (FIG. 4).

Together, these data show that in familial DCM, telomere shortening occurs. This clinical observation can be modeled using patient iPSC-derived cardiomyocytes in 30 days of culture. Furthermore, critically shortened telomeres in iPSC-CMs elicit a DNA damage response as measured by 53BP1 foci (FIG. 4). This activation of a DNA damage response represses mitochondrial biogenesis through a p53-mediated repression of the mitochondrial master regulator peroxisome proliferator-activated receptor gamma co-activator 1-alpha and 1-beta (PGC1α and PGC1β) that leads to mitochondrial dysfunction and subsequently dilated cardiomyopathy. Together, these data show that telomere length measurements in iPSC-CMs can serve as a novel biomarker to detect or monitor DCM.

Figure 5A:
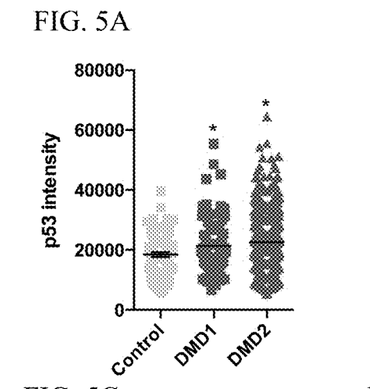
Figure 5B:
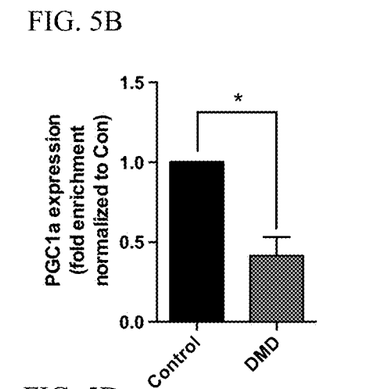
Figure 5C:
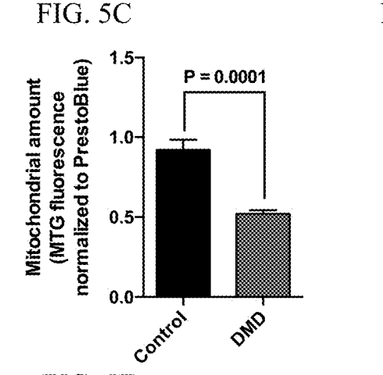
Figure 5D:
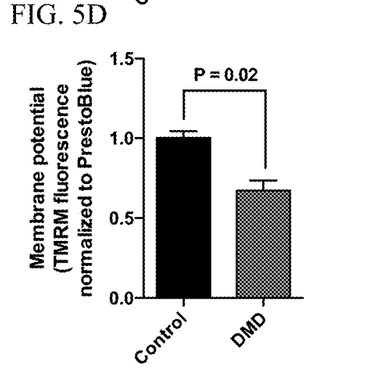
Figure 5E:
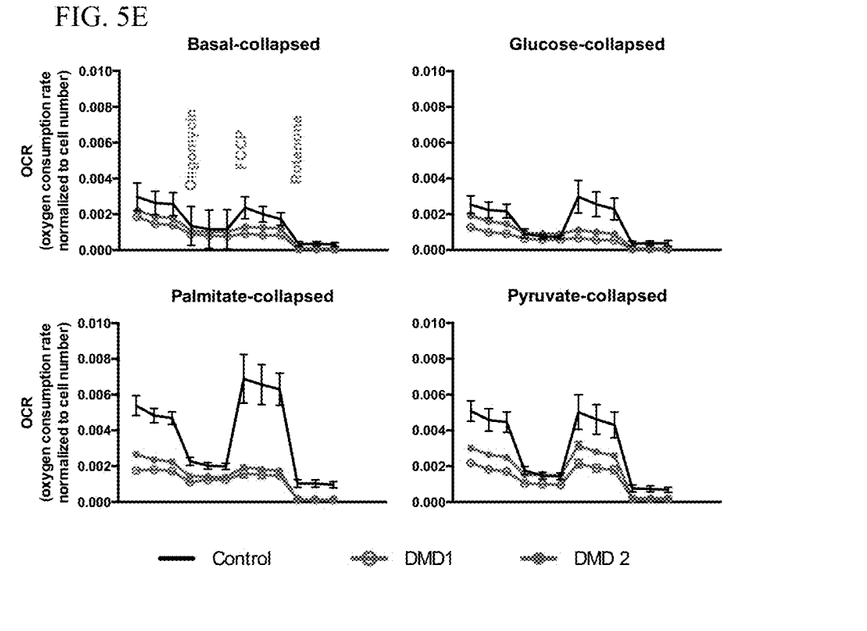

In FIG. 5 it is shown that in DMD hiPSC-CMs, there is a significant increase in DNA damage response p53 proteins by immunostaining (FIG. 5a). In DMD hiPSC-CMs there is a significant decrease in PGC1a mRNA (FIG. 5b), significant decrease in mitochondrial amount (FIG. 5c), a significant decrease in mitochondrial membrane potential (FIG. 5d) and a significant decrease in mitochondrial function as measured by real-time mitochondrial respiration (FIG. 5e) compared to control hiPSC-CMs. Critically short telomeres in DMD hiPSC-CM are therefore responsible for the onset of mitochondrial dysfunction—a hallmark of DCM.

These data demonstrate that telomere shortening occurs in contractile cells (cardiomyocytes) that require the expression of sarcomeric genes but not in non-contractile cells (vascular smooth muscle cells).

Methods

Human cardiac samples. Control hearts were isolated <24 h post mortem from de-identified male patients who succumbed to non-cardiac disease at University of British Columbia. The TNNT2 heart was isolated prior to heart transplant at Stanford University. The TTN hearts were obtained at Brigham and Women's Hospital/Harvard (Drs. Christine and Jon Seidman). The LMNA and matching donor hearts were obtained at INSERM, France (Drs. Gisele Bonne and Annie Laquerriere). All samples were subjected to the routine neutral-buffered formalin fixation followed by paraffin embedding. Sections (4 μm) from the paraffin blocks were placed on ChemMate slides (Fisher Scientific) for the telomere Q-FISH analysis. All protocols using human samples were reviewed and approved by the Stanford Institutional Review Board.

Telomere Q-FISH and Immunofluorescence and image acquisition. Cardiac paraffin sections were de-paraffinized in xylene and re-hydrated in serial ethanol concentrations. iPSC and iPSC-CMs were seeded 3 days prior to isolation on matrigel coated 8-chamber slides and fixed with 4% paraformaldehyde for 5 min at room temperature on day 30 of differentiation. Antigen retrieval was performed in citrate buffer (10 mmol l$^{-1}$ sodium citrate, pH 6.0) for 30 min in a steam cooker. Telomere Q-FISH was performed as previously reported using TelC probes Slides were blocked with staining buffer (4% calf serum/0.1%Triton X-100/PBS) and stained overnight at 4° C. with rabbit anti-53BP1 (1:400, Bethyl), washed with staining buffer and incubated with donkey anti-rabbit Alexa 647 secondary antibodies (1:400, Abcam). Next, the slides were stained with prediluted mouse anti-cardiac troponin t (Abcam ab74275) for 1 hr at room temperature, washed with PBS, incubated with goat anti-mouse Alexa 488 (1:400, Abcam) for 1 hr and counterstained with 1 μg ml$^{-1}$ DAPI solution in PBS for 5 min, washed with dH$_2$O, air dried and mounted with ProLong Gold Antifade (Life Technologies). Images were captured on a Nikon Spinning Disk Confocal microscope using the NIS-Elements program (Nikon). Relative telomere length normalized to DAPI stained nuclei was captured using ImageJ plugin Telometer as previously described. 53BP1 foci counting was carried out using CellProfiler.

Statistical analysis. All data are shown as the mean±SEM of multiple experiments. Statistical differences between more than two groups were analyzed with one-way analysis of variance (ANOVA) tests followed by Sidak's multiple comparison test. Statistical differences between two groups were tested using two-tailed Student's t test. Significant differences were determined when P value is less than 0.05.

Figure 6:
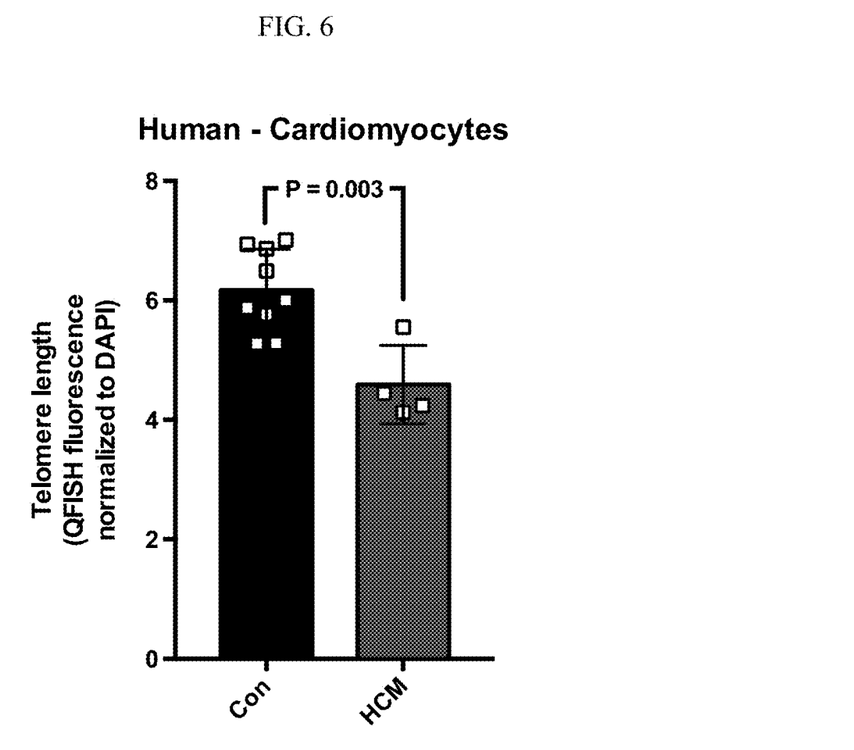
FIG. 6. HCM cardiomyocytes exhibit telomere shortening. Intensity of telomere staining relative to DAPI is shown for MYH7 (n=1), MYBPC3 (n=1), LAMP2 (n=1), TNNI3 (n=1) and healthy controls samples (n=9). The number of nuclei (N) scored: MYH7 (N=72), MYBPC3 (N=36), LAMP2 (N=58), and TNNI3 controls (N=32), and and controls (N=70, 69, 65, 124, 128, 121, 99, 214, and 220). Statistical differences in primary patient samples were tested using a two-tailed Student's t-test. Statistical differences between the hiPSC and hiPSC-CM groups were analyzed using one-way analysis of variance (ANOVA) tests followed by Sidak's multiple comparison test. All data are shown as the mean±SD. Significant differences were determined as P value <0.05.
Figure 7:
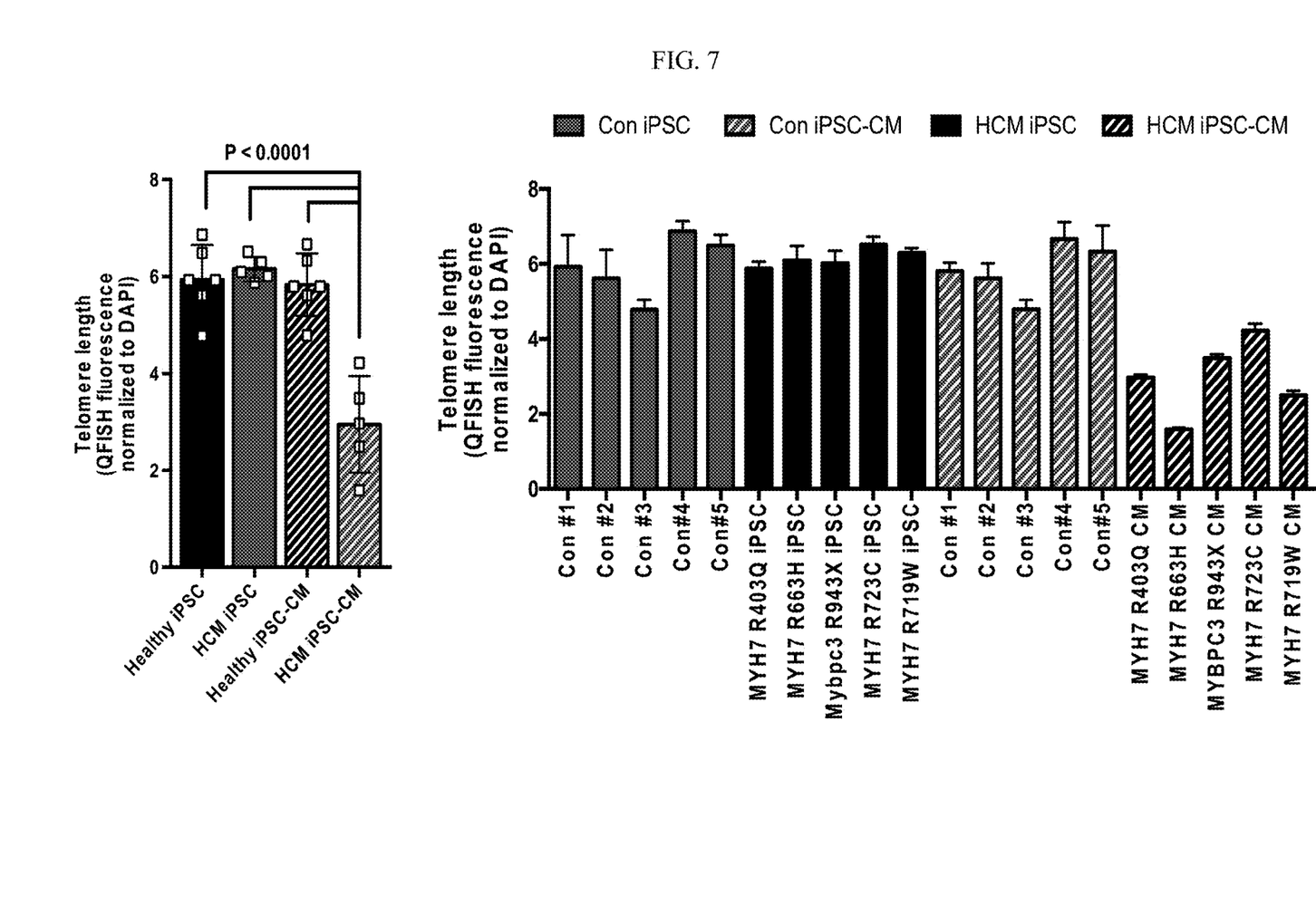
FIG. 7. HCM patient iPSC-CMs exhibit telomere shortening. Intensity of telomere staining relative to DAPI is shown for MYH7 (n=4), and MYBPC3 (n=1), and healthy controls samples (n=5). The number of nuclei (N) scored: MYH7 iPSC (N=117, 34, 65, and 89), MYH7 iPSC-CM (N=119, 115, 79, and 54), MYBPC3 iPSC (N=38), MYBPC3 iPSC-CM (N=37), control iPSC (N=111, 107, 55, 46, 77, and 111), and control iPSC-CM (N=92, 29, 44, 100, 210, and 92). Statistical differences in primary patient samples were tested using a two-tailed Student's t-test. Statistical differences between the hiPSC and hiPSC-CM groups were analyzed using one-way analysis of variance (ANOVA) tests followed by Sidak's multiple comparison test. All data are shown as the mean±SD. Significant differences were determined as P value <0.05.

| | Disease genotype |
|---|---|
| FIG. 1: DCM Patient cardiomyocyte telomere measurement | DMD from NCB 2013; TNNT2; TTN; LMNA |
| FIG. 2: DCM Patient vascular smooth muscle cell telomere measurement | DMD NCB 2013; TNNT2; TTN Not applicable (LMNA mutation does affect all cell types) |
| FIG. 3: DCM Patient iPSC and iPSC-derived cardiomyocyte telomere measurement | DMD; TNNT2; TTN |
| FIG. 4: DNA damage response: 53BP1 & p53 | DMD; TNNT2 |
| FIG. 5: Decreased PGC1a expression (mRNA level), Decreased mitochondrial amount/membrane potential/respiration | DMD |
| FIG. 6: HCM Patient cardiomyocyte telomere measurement | MYH7; MYBPC3; TNNI3; LAMP2 |
| FIG. 7: HCM patient iPSC and iPSC-derived cardiomyocyte telomere measurement | MYH7; MYBPC3 |

The culture of iPSC and derivation of cardiomyocytes from them is essentially as described by Burridge et al. (2016) Meth. Mol. Biol. 1353:119-130; and Burridge et al. (2015) Curr. Prot. Hum. Geneti. 87:21.3.1-21.2.15, with the following modifications.

Reagents:
Matrigel Corning (356231)
RPMI 1640 (Life Tech; 11875-093)
RPMI 1640 No Glucose (Life Tech; 11879-020)
Nutristem (Stemgent; 01-0005)
B27+Ins Supplement (Life Tech; 17504-044)
B27−Ins Supplement (Life Tech; A18956-01)
CHIR99021 (Selleck S1263, 5 mg)
IWR-1 (Sigma 10161, 5mg)
Y-27632 2HC1 (Selleck S1049, 5 mg)
Dissociation: Accutase (Life Tech; A1110501)

Thawing iPS from liquid nitrogen vials: Standard protocol requires freezing 3×10$^6$ cells per vial (1 well of a 6-well plate). Warm all media by leaving at room temperature for 10 min. 3 mL of Nutristem medium+thawed 1 mL cells into 15 mL test tube. Spin down at 1200 rpm for 5 min. Tilt the tube to aspirate. Add Rock Inhibitor in 1:2000 dilution (Stock is 10 mM, final is 5 uM) into Nutristem medium, prepare 2-2.5 mL per sample. Resuspend cells in 2.5 mL Nutristem medium using a 5 mL tip (no P1000) and seed into a 6-well. Once recovered, iPS cells should get confluent every 4 days (90% confluency, never allow 100%) and is split 1:6 to 1:10.

Normal passaging iPS: 1. Matrigel is 200×. Thaw on ice O/N. 900 uL of matrigel into 180 mL F10 can make roughly 15 6-well plates (1.5 mL per well). Dilute in F10 and coat plates at 37C for at least 30 minutes. 2. Seed iPSCs around 150,000 cells/well in a 6-wells plate. Add 2 mls of Nutristem and change medium every day. They should reach 90-100% confluency in around 4 days.

Differentiation: For differentiation, start with a 70-90% confluent well at the end of day 3-4 iPS culture, switch to RPMI 1640 with B27−Ins Supplement and add 4 uM, 6 uM or 8 uM of CHIR (Day 0). 4 mL Day 2—remove medium and replace with RPMI 1640+B27−Ins+5 uM IWR-1 2 mL. Day 4—remove medium and replace with RPMI 1640+B27−Ins. Day 6—remove medium and replace with RPMI 1640+B27+Ins. Day 8—remove medium and replace with RPMI 1640+B27+Ins. Day 10—to Day 30 remove medium and replace with RPMI 1640 No Glucose+B27+Ins+lactate.

Dissociate the beating iPSC-CMs on day 15-18 and re-plate to new wells with 2-wells into 1-well ratio. This step help to remove senescent fibroblasts during the glucose free treatment (day 10—day 30). If necessary, cells can be replated to chamber slides, glass bottom dishes or coverslips coated with matrigel for downstream assays.

The examples, which are intended to be purely exemplary of the invention and should therefore not be considered to limit the invention in any way, also describe and detail aspects and embodiments of the invention discussed above. The foregoing examples and detailed description are offered by way of illustration and not by way of limitation. All publications, patent applications, and patents cited in this specification are herein incorporated by reference as if each individual publication, patent application, or patent were specifically and individually indicated to be incorporated by reference. In particular, all publications cited herein are expressly incorporated herein by reference for the purpose of describing and disclosing compositions and methodologies which might be used in connection with the invention. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method of screening a candidate agent for activity in treating cardiomyopathy, the method comprising:
    determining the effectiveness of a drug on reducing the shortening of telomeres in human cardiomyocytes during in vitro differentiation,
    wherein the determining comprises:
    (i) measuring the length of the telomeres in cardiomyocytes that have not been contacted with the drug using quantitative in situ hybridization (QFISH), qPCR, telo-FISH, or Southern Blot,
    (ii) measuring the length of the telomeres in cardiomyocytes that have been contacted with the drug using quantitative in situ hybridization (QFISH), qPCR, telo-FISH, or Southern Blot, and
    (iii) comparing the length of the telomeres in cardiomyocytes that have been contacted with the drug with the length of the telomeres in cardiomyocytes that have not been contacted with drug to determine if the drug reduces shortening of telomeres;
    wherein the cardiomyocytes are differentiated in vitro from induced pluripotent stem cells derived from an individual with a genetic mutation in a sarcomeric protein selected from the group consisting of dystrophin (DMD), troponin T2 (TNNT2), lamin A (LMNA), and titin (TTN);
    wherein an effective drug reduces shortening of telomeres.

* * * * *